US00PP11883P2

(12) United States Plant Patent
Walden

(10) Patent No.: US PP11,883 P2
(45) Date of Patent: May 22, 2001

(54) MINIATURE ROSE PLANT NAMED 'JACHAL'

(75) Inventor: John K. Walden, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/399,641

(22) Filed: Sep. 20, 1999

(51) Int. Cl.[7] ..... A01H 5/00
(52) U.S. Cl. ..... Plt./125
(58) Field of Search ..... Plt./118, 125

*Primary Examiner*—Howard J. Locker
(74) *Attorney, Agent, or Firm*—Klarquist Sparkman Campbell Leigh & Whinston, LLP

(57) ABSTRACT

A miniature rose plant having deep yellow flowers of stable color and light, sweet fragrance; compact, dwarf growth habit; and dark green, glossy, disease resistant foliage.

1 Drawing Sheet

The present invention relates to a new and distinct variety of rose plant of the miniature class which was originated by me by crossing the variety JACyepat (not patented), with an unnamed seedling.

The primary objective of this breeding was to produce a new miniature rose variety having a flower 2 to 2¼ inches across, with deep yellow color that does not turn white as it ages, on a compact, dwarf plant with dark green, glossy and healthy foliage. The objective was substantially achieved, along with other desirable improvements, as evidenced by the following unique combination of characteristics that are outstanding in the new variety and that distinguish it from its parents, as well as from all other varieties of which I am aware:

1. Deep yellow, stable flower color;
2. Dark green, glossy, disease resistant foliage;
3. Compact, dwarf plant habit;
4. 2 to 2¼ inch open flowers; and
5. Light, sweet fragrance.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—JACyepat (not patented).

*Pollen parent.*—Unnamed seedling (AROyumi× unnamed seedling).

Classification:

*Botanical.*—*Rosa hybrida.*

*Commercial.*—Miniature rose.

FLOWER

Observations made from specimens grown in a garden environment at Somis and Wasco, Calif. from April 1994 through August 1999.

Blooming habit: Recurrent.

Bud:

*Size.*—⅝ to ¾ inches long when the petals start to unfurl.

*Form.*—The bud form is pointed ovoid.

*Color.*—When sepals first divide, bud color is Yellow Group 12B. When half blown, the upper sides of the petals are Yellow Group 12A. and the lower sides of the petals are Yellow Group 12B.

*Sepals.*—Color: Yellow-Green Group 145A. Surface texture: Smooth, with a few glandular structures. There are three normally appendaged sepals. There are two unappendaged sepals with hairy edges.

*Receptacle.*—Color: Yellow-Green Group 144A. Shape: Funnel. Size: Small (about ¼×¼ inch). Surface: Smooth.

*Peduncle: Length: Short (about* 1 to 1⅛ inches). Surface: Glandular. Color: Yellow-Green Group 146C. Strength: Stiff, erect; slender.

Bloom:

*Size.*—Small. Average open size is about two inches.

*Borne.*—Singly.

*Stems.*—Strength: Normal. Average length is about six to eight inches.

*Form.*—When first open: High centered. Permanence: Flattens.

*Petalage.*—*Number of petals under normal conditions:* 25–30.

*Color.*—The upper sides of the petals are Yellow Group 12A. The reverse sides of the petals are Yellow Group 12B. The major color on the upper side is Yellow Group 12A.

*Variegations.*—None

*Discoloration.*—The general tonality at the end of the first day: Yellow Group 12A. At the end of the third day: Yellow Group 12A. With further aging, color becomes Yellow Group 5C.

*Fragrance.*—Slight; myrrh.

Petals:

*Texture.*—Leathery.

*Shape.*—Oval; pointed.

*Form.*—Edges slightly quilled.

*Arrangement.*—Imbricated. Petaloids in the center are few (3 to 5); large.

*Persistence*.—Petals hang on an dry.

*Lastingness*.—On the plant: Very long (about 9 to 12 days). As a cut flower: Not tested.

Reproductive parts:

*Anthers*.—Size: Medium. Quantity: Many. Color: Yellow Group 12B. Arrangement: Regular around styles.

*Filaments*.—Color: Yellow Group 12B.

*Pollen*.—Color: Between Yellow Group 13A and Yellow Group 13B.

*Styles*.—Color: Between Yellow-Green Group 145C and Yellow-Green Group 145D.

*Stigmas*.—Color: Between Yellow-Green Group 145C and Yellow-Green Group 145D.

Plant:

*Form*.—Bush.

*Growth*.—Vigorous; dwarf; upright; compact. At maturity, height is 20 to 24 inches, width is 18 to 20 inches.

Foliage: Number of leaflets on normal mid-stem leaves: Seven.

*Size*.—Small (3 to 3½ inches long×1¾ inches wide).

*Quantity*.—Normal.

*Color*.—New foliage: Upper surface: Yellow-Green Group 146B and Greyed-Red Group 178B. Lower surface: Mostly Yellow-Green Group 146B and some Greyed-Red Group 178B. Old foliage: Upper surface: Green Group 137A. Lower surface: Yellow-Green Group 146B.

Leaflets:

*Shape*.—Broadly oval.

*Texture*.—Leathery; glossy.

*Edge*.—Serrated.

*Serration*.—Double.

*Petiole rachis*.—Color: Between Yellow-Green Group 146B and Yellow-Green Group 146A.

*Petiole underside*.—Smooth; with prickles.

*Stipules*.—Medium (about ¾ inch); serrated.

*Disease resistance*.—Resistant to mildew, blackspot and rust under normal growing conditions.

Wood:

*New wood*.—Color: Near Yellow-Green Group 146B with some Greyed-Red Group 178B. Bark: Smooth.

*Old wood*.—Color: Green Group 137A. Bark: Smooth.

Prickles:

*Quantity*.—On main canes from base: Ordinary. On laterals from main canes: Ordinary.

*Form*.—Short (about ¼ inch); hooked downward.

*Color when young*.—Between Greyed-Red Group 179C and Greyed-Red Group 179D.

*Color when mature*.—Near Greyed-Orange Group 174B.

Small prickles:

*Quantity*.—On main stalks: None. On laterals: None.

I claim:

1. A new and distinct variety of rose plant of the miniature class, substantially as herein shown and described, characterized particularly by its deep yellow flowers of stable color and light, sweet fragrance; compact, dwarf growth habit; and dark green, glossy, disease resistant foliage.

* * * * *

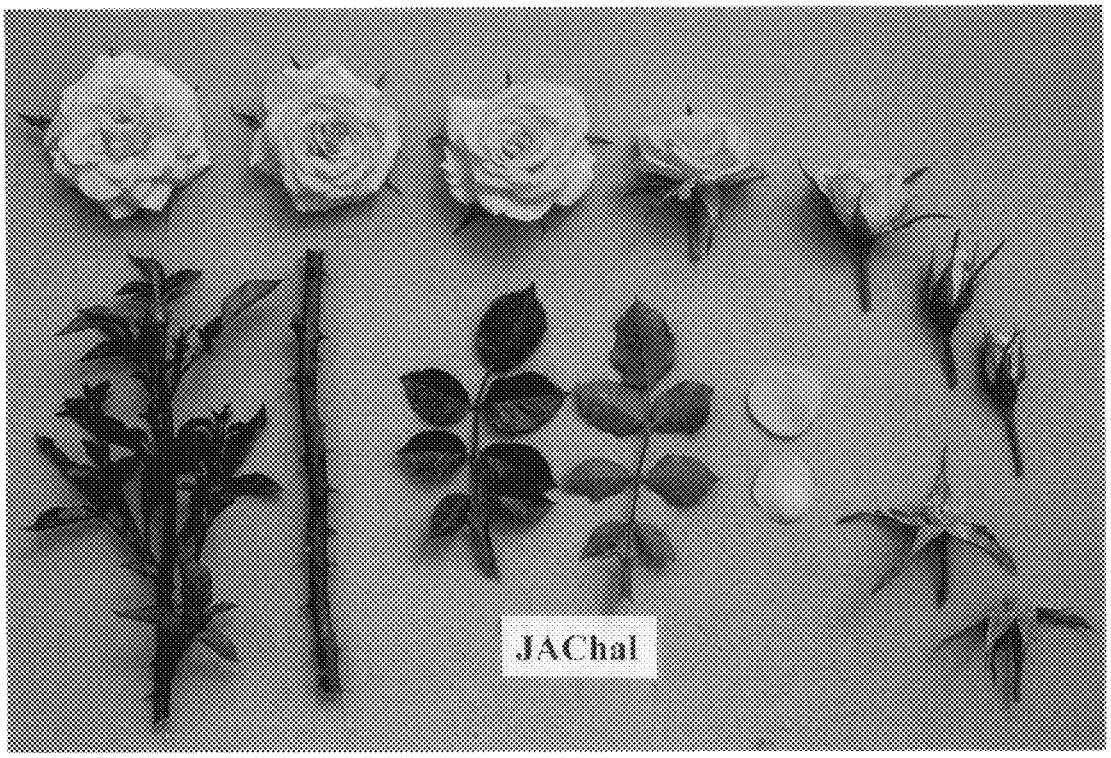
JAChal